(12) United States Patent
Mallwitz et al.

(10) Patent No.: US 7,323,119 B2
(45) Date of Patent: Jan. 29, 2008

(54) COLOR STABILIZATION OF HYDROQUINONE HYDROXYETHYL ETHER PRODUCTS

(75) Inventors: Jayne Mallwitz, Louisville, KY (US); Robert C. Hire, Dayville, CT (US); Kiran B. Chandalia, Fairfield, CT (US)

(73) Assignee: Arch Chemicals, Inc., Norwalk, CT (US)

( * ) Notice: Subject to any disclaimer, the term of this patent is extended or adjusted under 35 U.S.C. 154(b) by 275 days.

(21) Appl. No.: 11/259,849

(22) Filed: Oct. 26, 2005

(65) Prior Publication Data

US 2006/0043342 A1    Mar. 2, 2006

Related U.S. Application Data

(62) Division of application No. 10/883,071, filed on Jun. 30, 2004, now Pat. No. 6,994,804.

(60) Provisional application No. 60/484,872, filed on Jul. 2, 2003.

(51) Int. Cl.
*C09K 15/24* (2006.01)
*C09K 15/32* (2006.01)
*C07C 43/205* (2006.01)
*C07F 9/6574* (2006.01)
*C08K 5/52* (2006.01)

(52) U.S. Cl. .......................... 252/400.24; 252/182.27; 252/182.29; 252/182.31; 252/183.12; 568/580; 568/630; 524/120; 524/119

(58) Field of Classification Search ............ 252/400.24
See application file for complete search history.

(56) References Cited

U.S. PATENT DOCUMENTS

| | | | | | |
|---|---|---|---|---|---|
| 3,205,269 | A | * | 9/1965 | Friedman | 568/581 |
| 3,592,858 | A | * | 7/1971 | Brimer | 568/580 |
| 4,119,594 | A | * | 10/1978 | Iobst et al. | 528/57 |
| 4,383,051 | A | * | 5/1983 | Meyborg et al. | 521/176 |
| 4,731,410 | A | * | 3/1988 | Bueltjer et al. | 524/539 |
| 5,599,874 | A | * | 2/1997 | Singer et al. | 524/590 |

* cited by examiner

*Primary Examiner*—Joseph D. Anthony
(74) *Attorney, Agent, or Firm*—Wiggin and Dana LLP; Dale L. Carlson; Elizabeth A. Galletta

(57) ABSTRACT

The present invention relates to the color stabilization of hydroquinone hydroxyethyl ethers by phosphite compounds containing the bis-cyclic structure of spiro phosphites, both rings being attached to the same tertiary carbon atom in the phosphite molecule.

4 Claims, No Drawings

COLOR STABILIZATION OF HYDROQUINONE HYDROXYETHYL ETHER PRODUCTS

CROSS REFERENCE TO RELATED DOCUMENT

This patent application is a divisional of commonly owned U.S. patent application Ser. No. 10/883,071 entitled "Color Stabilization of Hydroquinone Hydroxyethyl Ether Products" that was filed on Jun. 30, 2004 now U.S. Pat. No. 6,994,804. Priority is herewith claimed under 35 U.S.C. §119(e) from co-pending U.S. Provisional Patent Application No. 60/484,872, filed Jul. 2, 2003, entitled "Color Stabilization Of Hydroquinone Hydroxyethyl Ether Products," by Jayne Mallwitz et al. The disclosure of this U.S. Provisional Patent Application is incorporated by reference herein in its entirety.

BACKGROUND OF THE INVENTION

1. Field of the Invention

The present invention relates to Hydroquinone di-(2-hydroxyethyl) ether, referred to as HQEE, which is widely used as a chain extender to make high performance polyurethane cast elastomers or thermoplastics elastomers in the polyurethane industry. The pure adduct of 2 moles of ethylene oxide (EO) and 1 mole of hydroquinone (HQ) is very crystalline and is believed to be desirable to get the best properties. However, for practical reasons, the pure adduct of 2 moles of EO and 1 mole of HQ is not available commercially. During ethoxylation of HQ with EO, due to kinetics, in addition to the desirable adduct, one also gets, mono adduct, triadducts, and higher adducts. In addition, the solvent used in the process also imparts impurities. Therefore, on a commercial scale, the HQEE grades available have 1-10% of non-desirable species and 99-90% of pure adduct (2 moles EO and 1 mole HQ). The impurities lower the final part properties and cause color instability for HQEE when HQEE is exposed to heat and/or oxygen. That is the color of HQEE goes up with time and temp. In many plants, HQEE is processed at elevated temp and there the color of HQEE goes up leading to parts, which are high in color. The color increase is very significant when light or pastel color parts are to be produced. Therefore, a practical method to stabilize the color of generally available grades of HQEE is desired and this invention provides such solution.

2. Brief Description of Art

It is well known that hydroquinone hydroxyethyl ethers (HQEE) are used for manufacturing of polyurethanes. Commercial grade hydroxyethyl ethers of hydroquinone contain >90% of hydroquinone bis (2-hyroxyethyl) ether. Due to the impurities contained in the product, they have tendency to discolor especially at higher temperatures. Hydroxyethyl ethers of hydroquinone are solids at room temperature and for application purposes are kept in molten condition. At increased temperature discoloration proceeds faster and there is a need for color stabilization to allow the use in color sensitive applications.

Color stabilization of hydroquinone hydroxyethyl ethers using phosphite type color stabilizer have been described in U.S. Pat. No. 3,592,858. According to the disclosure the phosphite molecule consists of either one or two cyclic phosphite groups attached to an aryl- or cycloalkyl ring. The result of color stabilization was not good enough to protect against discoloration for prolonged usage especially with commercial grades of hydroquinone hydroxyethyl ethers.

DETAILED DESCRIPTION OF THE INVENTION

Antioxidants are known to be color stabilizers for many products and processes involving exposure to oxygen or heat. Many general mechanisms as to how the antioxidants work have been proposed in the literature. However, a variety of factors such as polymer structure, polymer processing conditions, (time, temp, pressure), and antioxidant structure, decide which antioxidant or combination of antioxidants work the best. For the current problem on hand, several chemistries were evaluated as stabilizers for hydroquinone hydroxyethyl ether products (HQEE) including: phenolic based-2,6-di-t-butyl-p-cresol, Tetrakis[methylene (3,5-di-t-butyl-4-hydroxyhydroconnamate)]methane, 2,2-oxalydiamidobis[ethyl 3-(3,5-di-t-butyl-4-hydroxyphenyl)] propionate; acyclic phosphite based-Tris(2,4-di-t-butylphenyl)phosphite, Tris(nonylphenyl)phosphite; cyclic phosphite based-2,4,6-tri-t-butylphenyl 2 butyl 2 ethyl 1,3 propane diol phosphite and bis-cyclic phosphite based-Diisodecyl Pentaerythritol Diphosphite, Bis(2,4-di-t-butylphenyl)Pentaerythritol, Distearyl Pentaerythritol Diphosphite.

It has been surprisingly found, in accordance with the present invention, that phosphite compounds containing the double ring structure of bis cyclic phosphites, that are attached to the same tertiary carbon atom were very efficient in color stabilization of hydroquinone hydroxyethyl ethers and any present impurities. The phenolic-based antioxidants were found to afford no improvement in color stability and some of the products evaluated lead to an increased in color. In contrast to the prior art where the color stabilizer used was a phosphite, which had a molecule with either one cyclic phosphite group or two groups that were attached para on an aryl- or cycloalkyl ring the color stabilizer used according to the present invention have a spiro ring structure in which the two rings are attached to the same tertiary carbon atom. Color stabilization effect of the phosphite used in the previous art (U.S. Pat. No. 3,592,858) was found to show a slight improvement, but not sufficient to be used with commercial HQEE, the present inventors have surprisingly discovered that phosphite compounds containing double ring structure, which are attached to the same tertiary carbon atom in the phosphite molecule, are very efficient in color stabilization of hydroxylalkyl ethers of hydroquinone. Preferably such hydroxylalkyl ethers of hydroquinone contain >80% of pure adduct of 2 moles of EO and 1 mole of hydroquinone and most preferably contain >90% of pure adduct of 2 moles of EO and 1 mole of hydroquinone. Commercial hydroxyalkyl ethers of hydroquinone typically contain >90% of pure adduct of 2 moles of EO and 1 mole of hydroquinone and contain <10% of other species of which the triether (3 moles of EO and 1 mole of hydroquinone) is the predominant specie. Suitable phosphite compounds containing double ring structure of cyclic phosphates, which are attached to the same tertiary carbon atom in the molecule are phosphites like commercially available Weston 619F, and Doverphos 1220. The antioxidants of this type were evaluated to optimize the usage level that was determined to be between 0.2% to 3% and most preferably between 0.5 and 1.0%. It is believed that phosphite compounds containing double ring structure of cyclic phosphites, which are attached to the same tertiary carbon atom in the molecule have the optimal chemical structure. This is because two phosphite rings attached to the same tertiary carbon atom are in sterically stressed state The color stabilizing agents disclosed here can be added during the manufacturing of hydroxyalkyl ethers of hydroquinone or could be post added. If added during the manufacturing, they can help to produce a lower initial color product. Also, the polyurethane articles produced from color stabilized HQEE display lighter initial color and enhanced color stability.

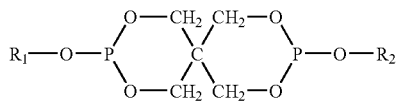

$R_1$ and $R_2$ can be aromatic ring with or without substituents $R_1$ and $R_2$ can be any akyl or cycloalkyl group $R_1$ and $R_2$ can be same or different The present invention is further described in detail by means of the following Examples and Comparisons. All parts and percentages are by weight and all temperatures are degrees Celsius unless explicitly stated otherwise.

EXAMPLE 1

Experimental Procedure: Commercial HQEE with the following analysis was used to evaluate the effectiveness of antioxidants. The analysis was Diether hydroquinone (2 moles EO plus 1 mole hydroquinone)-92%, Triether of hydroquinone (3 moles of EO plus 1 mole of hydroquinone)-7%, other-1%. To 14 gram samples of this HQEE, we initially compared the antioxidants of Table 1 by adding the antioxidant in an amount of 1% based on the weight of the mixture. The mixture was heated to 150 C, under nitrogen, and the colors of the mixtures were compared at 4 hours after mixing. The colors after 4 hours were compared using an approximation of the Gardner color for the molten HQEE material. The Gardner color results are given in Table 1 below. Table 2 below shows the results. As can be seen from Table 2, the most effective agents were Weston 619F (sample 2), and Doverphos 1220 (sample 10). As can be seen, for the 4 hours reading the control shows that the color goes up from 1 Gardner to 16 and for the additives of this invention, the color ranges between 1 to 2 Gardner.

TABLE 1

| AO | Chemistry | CAS # | Structure | Form | Gardner Color 4 hours at 150 C. |
|---|---|---|---|---|---|
| Weston 619F GE Specialty Chemicals | Distearyl Pentaerythritol DiphosphiteAliphatic-Bis cyclic phosphite | 3806-34-6 | 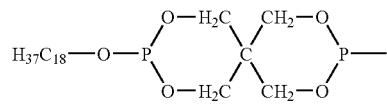 | Flakes | 1-2 |
| Naugard BHT Crompton | 2,6-di-t-butyl-p-cresol phenolic | 128-37-0 | | Powder | 16 |
| Irganox 1010 Ciba | Tetrakis[methylene (3,5-di-t-butyl-4-hydroxyhydroconnamate)] methane Phenolic | 6683-19-8 | | Powder | 16 |
| Wytox 312 Crompton | Tris(nonylphenyl)phosphite Aromatic-Acyclic phosphite | 26523-78-4 | 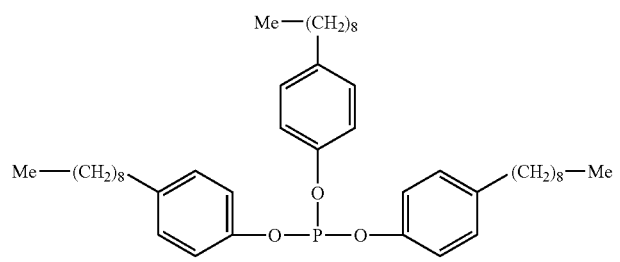 | Liquid | 10 |
| Naugard 492 Crompton | Phenolic-organic Acyclic phosphate blend | Not disclosed | | Liquid | 6-7 |
| Naugard XL-1 Crompton | 2,2-oxalydiamido-bis[ethyl 3-(3,5-di-t-butyl-4-hydroxyphenyl) propionate] Phenolic-based | 70331-94-1 | | Powder | 8 |

TABLE 1-continued

| AO | Chemistry | CAS # | Structure | Form | Gardner Color 4 hours at 150 C. |
|---|---|---|---|---|---|
| Naugard 524 Crompton | Tris(2,4-di-t-butylphenyl) phosphite Aromatic-Acyclic phosphite | 31570-04-4 | 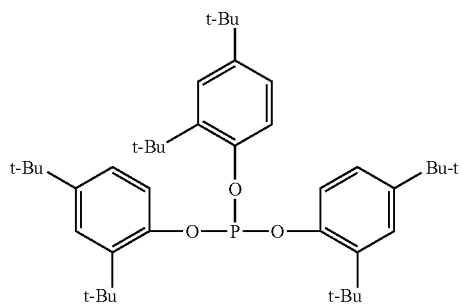 | Powder | >18 |
| Doverphos 1220 Dover Chemicals | Diisodecyl Pentaerythritol Diphosphite. (cyclic bis phosphite) | 26544-27-4 | 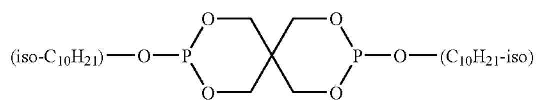 | Liquid | 1-2 |

TABLE 2

| Sample | Antioxidant | Initial HQEE Gardner Color | HQEE Gardner Color- 4 hours at 150 C. |
|---|---|---|---|
| 1 | None—Control | 1 | 16 |
| 2 | Weston 619F | 1 | >1 but <2 |
| 3 | Naugard BHT | 1 | 16 |
| 4 | Irganox 1010 | 1 | 16 |
| 5 | Wytox 312 | 1 | 10 |
| 6 | Ultranox 641 | 1 | 5 |
| 7 | Naugard 492 | 1 | 6-7 |
| 8 | Naugard XL-1 | 1 | 8 |
| 9 | Naugard 524 | 1 | >18 |
| 10 | Doverphos 1220 | 1 | >1 but <2 |

Notes:
1 is the control sample without any antioxidant;
2 and #10 are preferred examples of the invention;
3, #4, #5, #7, #8 and #9 are comparative examples.
And #6 is an example from prior art patent # 3,592,858.
HQEE Color—approximate Gardner color for molten HQEE While the invention has been described above with reference to specific embodiments thereof, it is apparent that many changes, modifications, and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. In an improved process for preparing a di-hydroxyalkylether of hydroquinone, the improvement comprising adding a discoloration inhibiting effective amount of a bis cyclic phosphite compound according to the formula

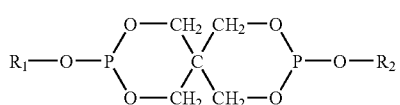

$R_1$ and $R_2$ can be aromatic ring with or without substituents
$R_1$ and $R_2$ can be any akyl or cycloalkyl group
$R_1$ and $R_2$ can be same or different
to a reaction mixture suitable for making said di-hydroxyalkylether of hydroquinone.

2. In an improved process for the color stabilization of a di-hydroxyalkylether of hydroquinone, the improvement comprising adding a discoloration inhibiting effective amount of a his cyclic phosphite compound according to the formula

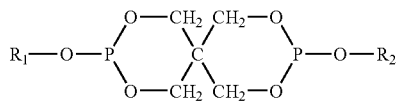

$R_1$ and $R_2$ can be aromatic ring with or without substituents
$R_1$ and $R_2$ can be any akyl or cycloalkyl group
$R_1$ and $R_2$ can be same or different
to the di-hydroxyalkylether of hydroquinone.

3. A polyurethane-forming reaction mixture comprising a di-hydroxyalkylether of hydroquinone and a discoloration inhibiting effective amount of a bis cyclic phosphite compound having the formula

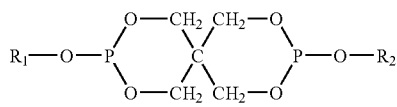

$R_1$ and $R_2$ can be aromatic ring with or without substituents
$R_1$ and $R_2$ can be any akyl or cycloalkyl group
$R_1$ and $R_2$ can be same or different.

4. A cast elastomer or thermoplastic elastomer made by reacting the reaction mixture of claim 3.

* * * * *

UNITED STATES PATENT AND TRADEMARK OFFICE
CERTIFICATE OF CORRECTION

PATENT NO. : 7,323,119 B2 Page 1 of 1
APPLICATION NO. : 11/259849
DATED : January 29, 2008
INVENTOR(S) : Mallwitz et al.

It is certified that error appears in the above-identified patent and that said Letters Patent is hereby corrected as shown below:

Column 6, line 33, change "his" to --bis--.

Signed and Sealed this

Eighth Day of July, 2008

JON W. DUDAS
*Director of the United States Patent and Trademark Office*